United States Patent [19]

Chen

[11] Patent Number: 4,621,642

[45] Date of Patent: Nov. 11, 1986

[54] MICROWAVE APPARATUS FOR PHYSIOTHERAPEUTIC TREATMENT OF HUMAN AND ANIMAL BODIES

[75] Inventor: Zu-fan Chen, Beijing, China

[73] Assignee: North China Research Institute of Electro-Optics, Beijing, China

[21] Appl. No.: 711,847

[22] Filed: Mar. 14, 1985

[30] Foreign Application Priority Data

Feb. 26, 1985 [GB] United Kingdom ................ 8504935

[51] Int. Cl.$^4$ ............................................ A61N 5/04
[52] U.S. Cl. ..................................... 128/422; 128/804
[58] Field of Search ............................... 128/422, 804

[56] References Cited

U.S. PATENT DOCUMENTS

| 3,670,737 | 6/1972 | Pearo | 128/422 |
| 3,924,196 | 12/1975 | Takahashi et al. | 128/804 |
| 4,108,147 | 8/1978 | Kantor | 128/804 |
| 4,204,549 | 5/1980 | Paglione | 128/804 |
| 4,271,848 | 6/1980 | Turner et al. | 128/804 |
| 4,346,715 | 8/1982 | Gammell | 128/422 |
| 4,403,618 | 9/1983 | Turner et al. | 128/804 |
| 4,448,198 | 5/1984 | Turner | 128/804 |

OTHER PUBLICATIONS

Paglione et al, "Microwave Applicators for Localized Hyperthermia Treatment of Malignant Tumors" *Conf.: Technology Growth for the 80's, 1980 IEEE MIT-S International Microwave Symposium Digest*, Washington D.C. USA, May 28-30 1980, pp. 351-354.

Chen et al., "An Apparatus for Microwave Acupuncture Treatment," *ACTA Electronica Sinica*, No. 1, Jan., 1982, pp. 82-83.

"Ancient Chinese Exercises Evaluated by Modern Thermography," *The Infrared Observer*, No. 2/80, p. 16.

Primary Examiner—William E. Kamm
Assistant Examiner—Mitchell J. Shein
Attorney, Agent, or Firm—Jeffrey H. Ingerman

[57] ABSTRACT

A wide bandwidth multifrequency direct contact type microwave physiotherapeutic apparatus for replacing acupuncture therapy in medical and hygenic practice is provided. The apparatus comprises a microwave generator with a multifrequency output varying within a range of 100–3,000 MHz, and an applicator made up of an inner conductor and an outer conductor, both of which maintain direct contact with skin during treatment. The outer conductor also serves as a screening structure. The conductors are shaped to ensure a good impedance match between the applicator and the human body and to avoid microwave leakage to the environment.

11 Claims, 9 Drawing Figures

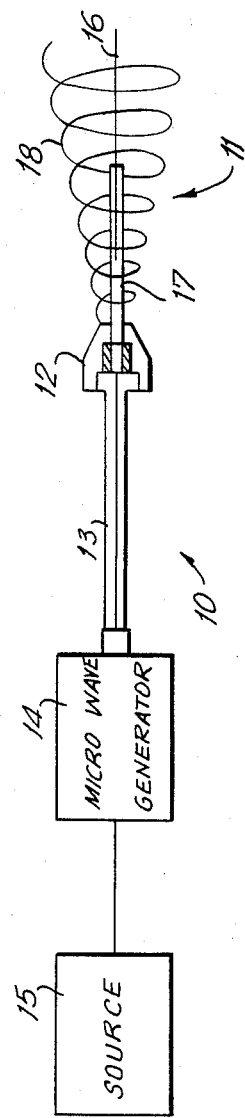
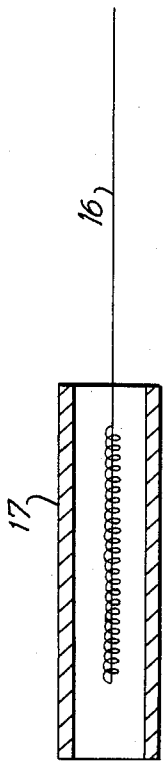
FIG.1
FIG.2

MICROWAVE APPARATUS FOR PHYSIOTHERAPEUTIC TREATMENT OF HUMAN AND ANIMAL BODIES

FIELD OF THE INVENTION

The present invention relates to an apparatus for localized treating of the human and animal body using multifrequency composite microwave radiation, which can substitute for traditional acupuncture therapy in medicine and hygiene.

BACKGROUND OF THE INVENTION

There are various kinds of known microwave apparatus having different structures and characteristics, operating by different processes and methods, yet having the common feature of using the heating effect induced in living tissue by microwave radiation to realize medical results. Therefore, they are used mainly in thermal treatment, hyperthermia and diathermy—for example, in the treatment of cancer.

In recent years, Chinese researchers have put forward some new ideas on the physical effects of microwave radiation on the human body. They believe that in addition to the thermal and nonthermal effects, there is a third effect produced during the microwave treatment of the human body, namely the regulating effect on the "jingluo" system or the channels-and-collaterals system of the human body. These ideas are based on the results of research work on the "jingluo" theory of traditional Chinese medicine, the mechanism of Qi Gong and Qi Gong therapy.

According to the theory of traditional Chinese medicine, there is a jingluo system inside the human body, coexisting with the other physiological systems, with anatomic structure like that of the circulatory system, nervous system, etc., which has not been proved by anatomy. A kind of "Qi", or vital energy, moving along the jingluo determines the conditions of human health. The jingluo are distributed throughout the human body in their own way, having specific positions, called the "acupoints" or "points", formed along them for acupuncture treatment. It is according to this theory that the acupuncture therapy selects different points to cure a wide variety of diseases and illnesses in medical and hygienic practice. Another practice related to the same theory is Qi Gong, a kind of deep breathing exercise. Having been trained at and taken up the exercise for a long time, a Qi Gong master can reach such a state that when he concentrates through the exercise, he can use his mind to control the movement of the vital energy along the jingluo through his body, and thus keep himself in good health. Some masters can even emit the vital energy through a certain point, called the "Fa Gong" or energy emitting point. Such a master can cure a patient by emitting the energy through this point, for example on his hand, to a selected point on the patient's body. This clinical practice of energy emitting therapy or Qi Gong therapy has long been practiced and widely acknowledged in China. Nevertheless, there are only a few Qi Gong masters who can reach such a state, and therefore the therapy cannot be applied widely.

Some researchers believe that there is some relationship between the jingluo system and the electromagnetic field of the human body. By studying the energy emitting phenomena with the help of modern instruments, researchers have detected at the energy emitting point the existence of wide band infrared radiation and low frequency subsonic waves, enhancement of magnetic field density, and concentration of the static electric field. The results of relevant tests performed by the present applicant were published in a report on page 16 of *The Infrared Observer*, No. 2/80.

In light of the aforesaid results, some researchers believe that the health of human beings may be improved by regulating the electromagnetic field of the human body through various methods of stimulating the points, such as acupuncture, energy emission, etc. Because microwave radiation can penetrate deep into the body and produce many kinds of physical effects, it is believed that the stimulation of the points by microwave radiation can achieve effects similar to that of acupuncture, moxibustion and Qi Gong therapy. As the biological electromagnetic field is characterized by continuous distribution and fluctuation, multifrequency composite microwave radiation should be used for point treatment, with concentrated microwave energy irradiating local surface areas of the human body, so that beneficial results of physical treatment similar to that of acupuncture and Qi Gong therapy not yet obtainable by prior microwave treatment can be obtained.

The present applicant previously developed an apparatus for microwave acupuncture treatment, published in an article on page 82 of January, 1982 issue of *ACTA ELECTRONICA SINICA*. The apparatus consists of an acupuncture antenna and a microwave generator. The said antenna includes an outer conductor which is a spiral-shaped wire and an inner conductor which is an acupuncture needle. The needle is inserted into a selected point during treatment and the spiral wire is kept contact with the skin around the point. The said inner and outer conductors are coupled with the human body directly while microwave radiation is emitted quantitatively and directionally to the point. Statistical analysis of the results of clinical practice have shown that this apparatus is more effective than traditional acupuncture therapy. It has been well accepted and has achieved commercial success, and it was awarded a gold medal at the fortieth Plovdiv International Technology Exhibition held in Bulgaria in 1984.

However, some patients do not like to receive the treatment because of the pain caused when the needle is inserted. This remains a difficult problem in traditional acupuncture therapy as well. Moreover, the fixing of the antenna during treatment makes some patients uneasy. In addition, there exists considerable leakage during operation from the spiral outer conductor of the microwave antenna. The difficulty encountered in matching the output impedance of the antenna with that of the human body further reduces the efficiency of the apparatus. Further, the output frequency range of the microwave generator is limited leading to fewer frequency components in the composite wave which is undesirable for achieving a multifrequency composite wave output, which is a requirement put forward by the original design. Finally, the design of the antenna described above limits the use of the apparatus to acupuncture treatment only.

SUMMARY OF THE INVENTION

The present invention is an improvement of the aforesaid apparatus for microwave acupuncture treatment. A new microwave applicator is provided, comprising an inner conductor which is a metal bar and a screening outer conductor formed around the inner conductor with one open end. The two conductors are fixed on the same base structure, insulated from each other, and connected respectively through the base with the inner and outer conductors of a coaxial cable. The end of the metal bar and the open end of the screening structure together form the therapeutic head of the microwave applicator and the head directly contacts the skin during treatment, with the outer conductor forming a screening structure. The present invention improves the original microwave generator in that its output frequency bandwidth is extended to the range of 100–3,000 MHz, and the number of components comprising its multiwave output is increased. In order to achieve an impedance match between the applicator and the human body, for all frequency components, the said outer conductor is designed into a special geometric shape, which increases the output efficiency, reduces the microwave leakage, and substantially avoids microwave interference with the environment. This applicator of direct-contact style retains the benefits of acupuncture while diminishing the pain and the danger of cross-infection of the patient. Furthermore, it limits the area and dosage of irradiation, thus causing no side effect to the patient. Since the applicator can be easily fixed onto the right place on the human body, it allows the patient to move slightly during treatment. By changing the dimensions of the inner and outer conductors, the applicator can be used in hyperthermia and diathermy. The inner conductor can also be replaced by a needle in treatment, thus maintaining all the merits of the original microwave acupuncture apparatus. The present invention can also be used for treatment of animals according to the same principal.

BRIEF DESCRIPTION OF THE DRAWINGS

FIG. 1 illustrates schematically the apparatus for microwave acupuncture treatment of the prior art;

FIG. 2 illustrates schematically the inner conductor of the antenna of the microwave acupuncture apparatus shown in FIG. 1;

DETAILED DESCRIPTION OF THE INVENTION

Figure 3:
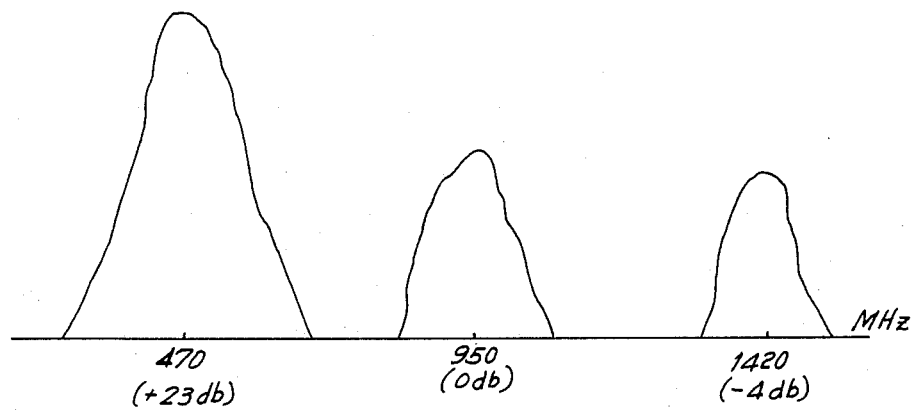
FIG. 3 illustrates the output frequency distribution of the apparatus shown in FIG. 1.

FIG. 1 illustrates schematically the apparatus for microwave acupuncture treatment of the prior art, wherein the said apparatus 10 comprises an acupuncture antenna 11, a coaxial cable 13, a microwave generator 14 and a power source 15. The acupuncture antenna has a base 12, an outer conductor of spiral shaped wire 18, an inner conductor formed from a tube 17 and a needle 16. The inner conductor 17 and the outer conductor 18 are insulated from each other, and the handle of the needle 16 is situated inside the tube of the inner conductor, as shown in FIG. 2. When giving a physiotherapeutic treatment, the needle is first inserted into a point, then the handle of the needle is slipped into the inner conductor 17 to form a capacitive coupling between them, while keeping the outer conductor in contact with the skin around the point. The power source 15 can be any kind of DC source and the output power of the antenna is controlled by adjusting the output voltage of the source. The output frequency distribution of the microwave generator 14 is shown in FIG. 3.

Figure 4:
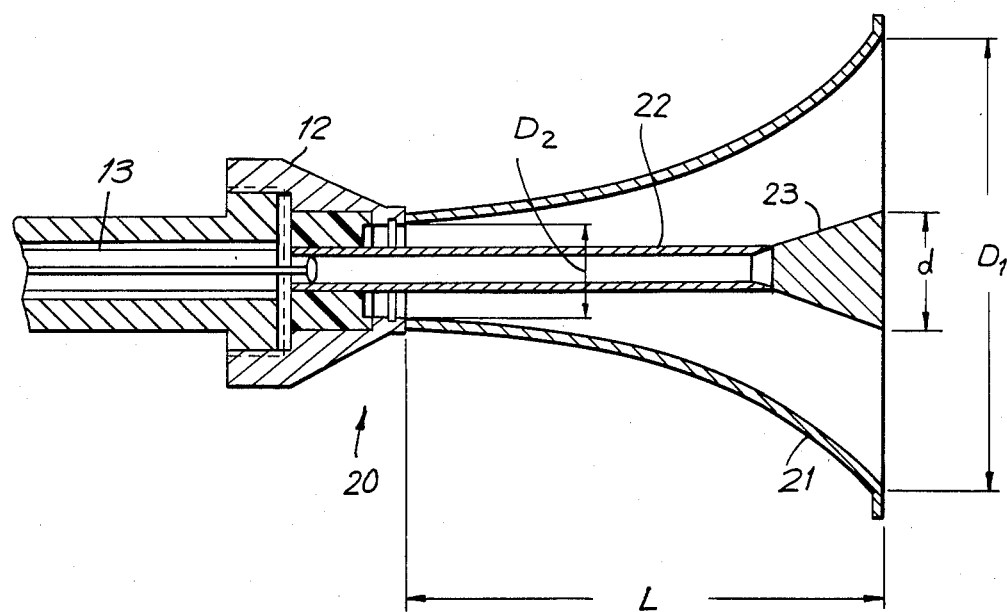
FIG. 4 illustrates schematically the microwave applicator according to this invention.

FIG. 4 shows the microwave applicator of this invention. The applicator 20 comprises an outer conductor 21, an inner conductor 22 and a base 12. The base 12 and the coaxial cable 13 connected with it are similar to that shown in FIG. 1. One end of the inner conductor 22 is fixed on the base 12 and is connected to the inner conductor of the cable 13 while the other serves as a physiotherapeutic head 23, which is made of metal and can be separated from the inner conductor 22. The outer conductor 21 is also fixed on the base 12 and is connected to the outer conductor of the cable 13. The inner and outer conductors 21 and 22 are insulated from each other. The outer conductor 21 expands exponentially from the base end to the open end to provide a good impedance match between the applicator and human body at all frequencies of the composite wave. The cross section of the outer conductor can be any form of a closed curve, but preferably that of a circle. When the cross section of both the inner and outer conductors are circular, as shown in FIG. 4, with $D_1$ representing diameter of the open end of the outer conductor, $D_2$ representing diameter of the base end of the outer conductor, L representing length of the outer conductor, and d representing diameter of the physiotherapeutic head of the inner conductor, the shape of the outer conductor can then be determined by the following equation:

$$y = ae^{bx}$$

wherein
$a = D_2/2$
$b = (1/L)ln(D_1/D_2)$

When the shape of the outer conductor has been determined, the output impedance of the applicator can be calculated by the following equation:

$$Z_o = (60/\sqrt{\epsilon})ln(D_1/d)$$

wherein $\epsilon$ represents dielectric constant of the skin. In practical use, $D_2$ can be determined from the dimensions of the coaxial cable and the conventional connector selected, L can be of any value chosen mainly for the purpose of convenience, while $D_1$ and d are determined by the use and the position of treatment on the body and can be changed at any time. The preferred ranges of their dimensions are as follows:
d: 0.1–45.0 mm
$D_1$: 10–200 mm.

Figure 5:
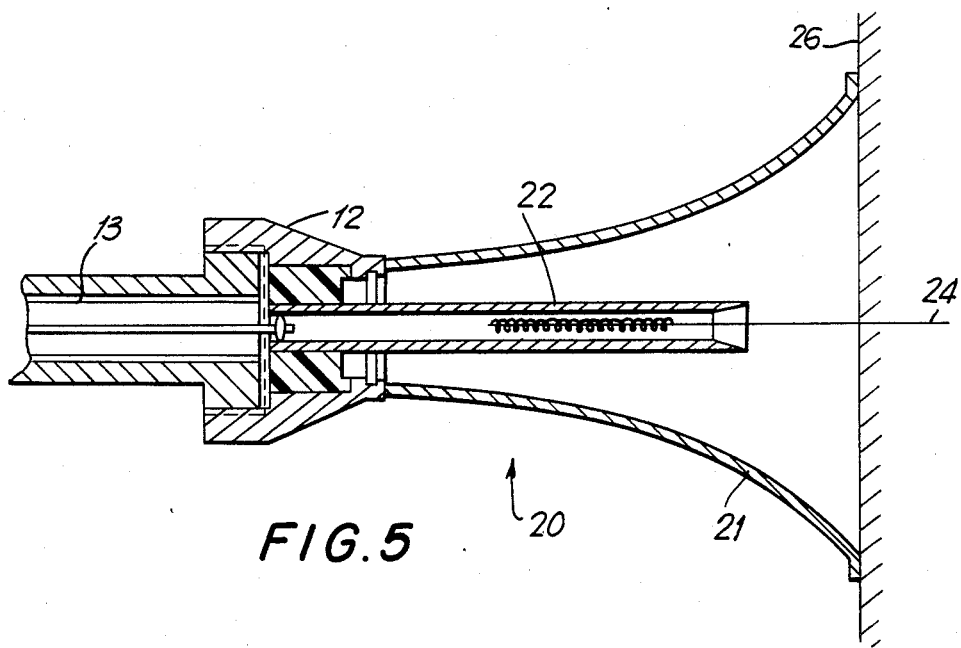
FIG. 5 illustrates schematically the applicator used together with a needle.
Figure 6:
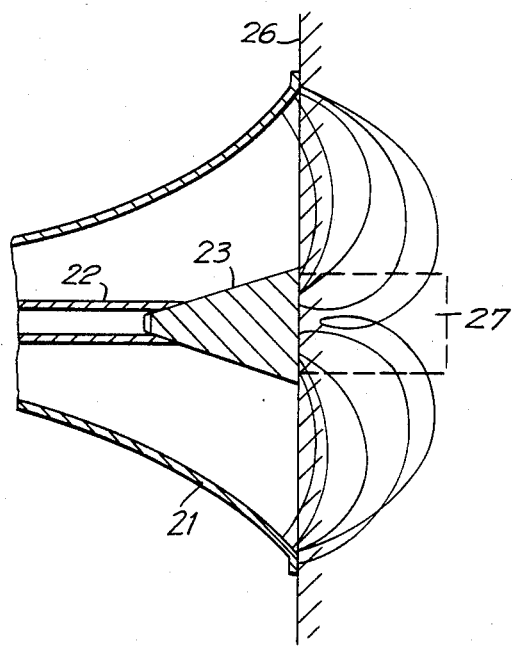
FIG. 6 illustrates the distribution of the electromagnetic field of the applicator when it is working.

When a physiotherapeutic head 23 with a d of a small value is used to radiate microwave energy to a point, a localized area of high density electromagnetic field is formed, as shown in FIG. 6 where the physiotherapeutic head 23 contacts with the skin, and the microwave energy radiated on this area will go deep into the body. In addition, since the output from the head 23 is a composite wave of multifrequency, the depth of penetration of each frequency component differs from one another. As a result, a vertical distribution of stimulation at the point is formed, which enables this apparatus to obtain, without the use of a needle, an effect very similar to that of acupuncture. The apparatus can be used to replace the conventional acupuncture therapy with a similar curative effect by providing the said inner conductor with a head of small d. When an applicator with large $D_1$ and d is used, an electromagnetic field of a relatively even density forms, enabling the apparatus to be used in hyperthermia and diathermy. For patients preferring the acupuncture treatment, the apparatus can be used in combination with an acupuncture needle in place of the head 23, as shown in FIG. 5. With the use of the present apparatus, the patient can receive simultaneously the effects of acupuncture, moxibustion, hyperthermia and diathermy as a result of the combined heating effect and skin effect. Preliminary statistical results of clinical practice have proven that this combined physiotherapeutic treatment is more effective than the conventional acupuncture treatment. Moreover, owing to the screening effect of its outer conductor and the good impedance match between the applicator and the human body, the present apparatus, as compared with the microwave acupuncture antenna of spiral wire outer conductor of the prior art, has a smaller output loss and almost no microwave interference with the environment. In addition, the capacitive coupling between the inner conductor and the needle provides at the point of the needle a relatively strong discharge which produces a localized high temperature area. Such a feature enables the present apparatus to be used for other medical purposes, such as, for example, the thermal treatment of cancer.

Figure 7:
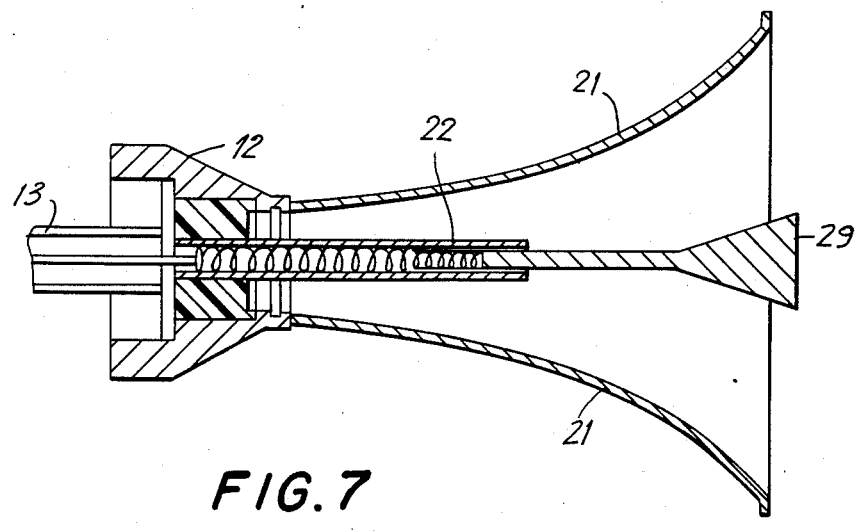
FIG. 7 illustrates another embodiment of the applicator.

FIG. 7 shows another embodiment of this invention, wherein the physiotherapeutic head 29 has an elastic connection with the inner conductor 22. The advantage of this design is that during treatment the inner conductor is kept in close contact with the point to provide a good match between the applicator and the body. This design is particularly useful for such special point as those on hands, and for very thin patients. In both embodiments one or more slots can be opened vertically on the outer conductor for the escape of moisture, such as sweat.

Figure 9:
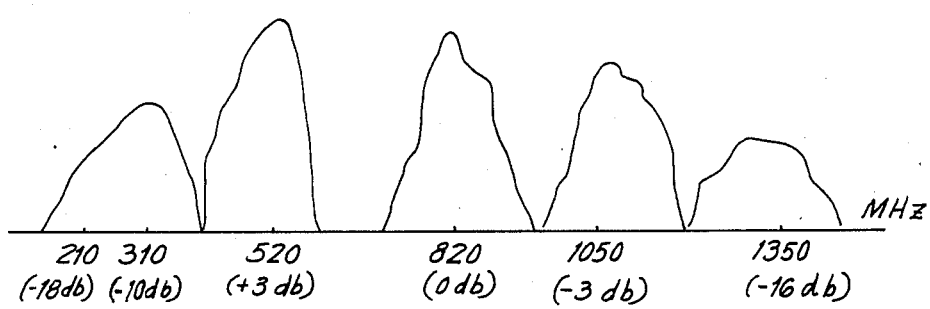
FIG. 9 illustrates the output frequency distribution of the apparatus shown in FIG. 8.
Figure 8:
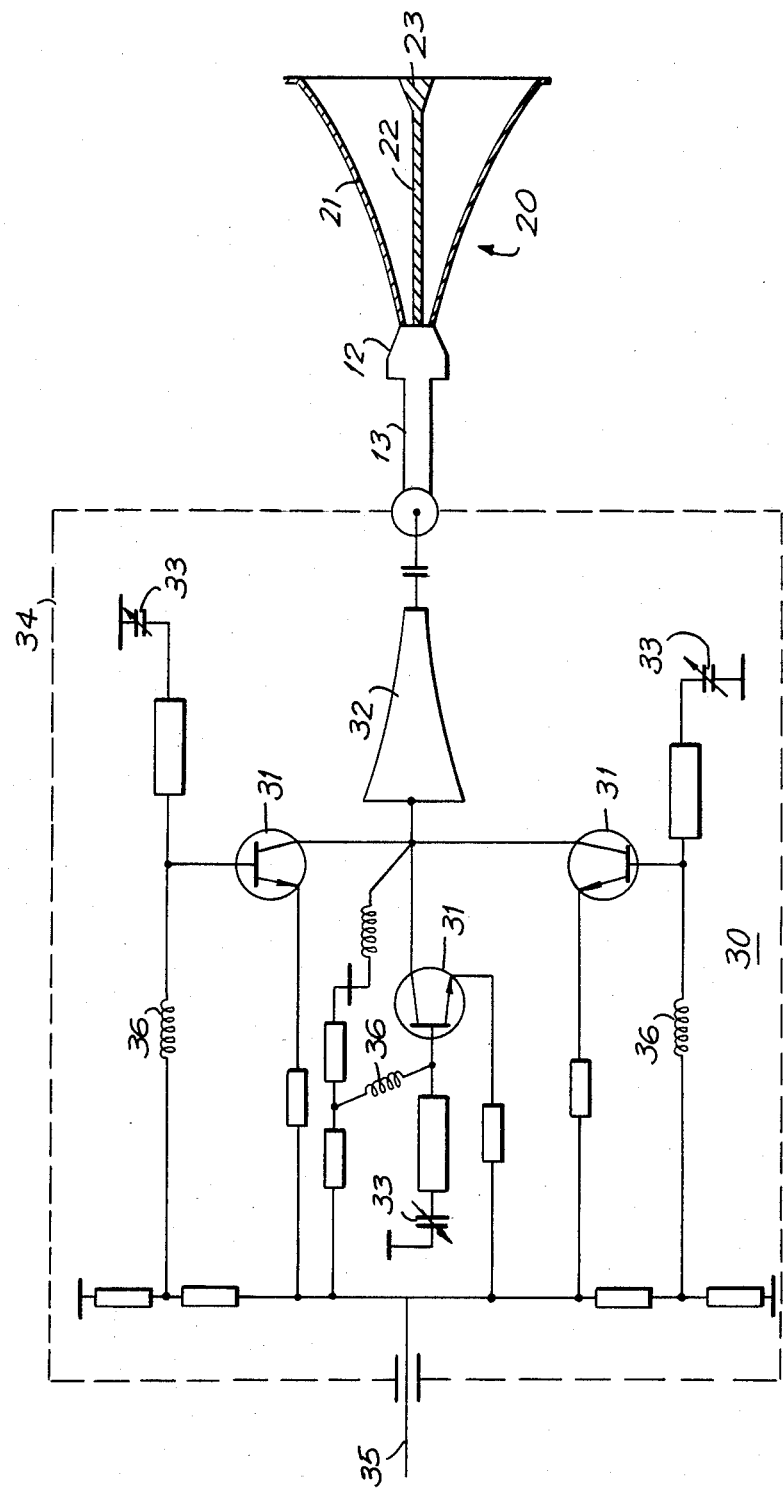
FIG. 8 illustrates an embodiment of the invention including a microwave generator and an applicator connected together.

FIG. 8 shows the circuit structure of the invention, wherein the applicator 20 can be any one shown in FIGS. 3, 5 and 7. The microwave generator 30 comprises three transistor oscillators connected in parallel and an impedance transformer 32. The three transistors 31 can be of the same or different type. The impedance transformer 32 is a microstrip impedance transformer, which is connected between the oscillators and the coaxial cable 13. The width of the transformer decreases exponentially from the oscillator end to the cable end. This ensures a good match at all frequencies of the composite wave. Oscillating frequency can be changed, by adjusting the parameters of the inductors 36 and/or the variable capacitors 33, within the range 100–3,000 MHz. The oscillating frequencies of the three oscillators differ from one another. The simultaneously parallel output of the three oscillators through the impedance transformer 32 makes possible the multifrequency output of the apparatus. The output frequency profile of this apparatus is shown in FIG. 9 which is only an example and the profile can be modified by regulating circuits parameters. According to FIG. 8, the number of frequency components can be increased by increasing the number of parallel oscillators within the cost-effective range. The present invention can be carried out by replacing the transistor oscillators with other component parts, such as, for example, integrated circuits. The microwave generator 30 in FIG. 8 is connected to a DC source through lead 35 and the ground in the circuit. The DC source can be a battery or a stabilized DC source and the adjustment of the DC voltage by conventional methods can change the output power of the apparatus within a range of 0.1–3 watt. The dashed line in FIG. 8 represents a grounded metal layer which provides good screening for the generator, avoids microwave interference with the environment and reduces the level of microwave radiation received by the operators. At the same time, it serves as a heat sink for the microwave generator as well.

One skilled in the art will recognize that the present invention can be practiced by other than the described embodiments, which are presented for the purposes of illustration and not of limitation, and the present invention is limited only by the claims which follow.

What is claimed is:

1. A microwave apparatus for regulating physiological functions of human and animal bodies, comprising:
   a microwave generator and a microwave applicator connected to said generator for emitting microwaves to a localized area on a body, wherein said applicator comprises inner conductor means and outer conductor means for noninvasively maintaining direct contact with the skin during treatment, said outer conductor means further serving as a screening structure.

2. The apparatus of claim 1 wherein said applicator comprises an inner conductor means formed from a metal bar connected at one end thereof to the output line of said generator, the other end thereof serving as a physiotherapeutic head, and an outer conductor means of a screening structure connected at one end thereof to the ground of said generator and opened at the other end thereof, said inner conductor means being held inside said structure of the outer conductor means.

3. The apparatus of claim 2 wherein the width of said outer conductor means increases exponentially from the end connected to said generator to the open end and has a cross section in the form of any substantially closed curve.

4. The apparatus of claim 3 wherein the cross section of said outer conductor means is circular and the width of said outer conductor means increases according to an exponential curve conforming the following equation:

$$y = ae^{bx}$$

wherein
   $a = D_2/2$,
   $b = (1/L)\ln(D_1/D_2)$,
   $D_1$ represents the diameter of said open end of said outer conductor means, $D_2$ represents the diameter of the other end of the outer conductor means, and L represents the length of said outer conductor means.

5. The apparatus of claim 7 wherein both said inner conductor means and said outer conductor means have circular cross sections, and the diameter, d, of said physiotherapeutic head is within the range of from 0.1 mm to 45.0 mm and the diameter, $D_1$, of said open end is within the range of from 10 mm to 200 mm.

6. A microwave apparatus for regulating physiological functions of human and animal bodies, comprising:

a microwave generator, said generator comprising a plurality of oscillators of different frequencies connected in parallel, having a common output line connected to said applicator for emitting multiwaves within a frequency range of from 100 MHz to 3,000 MHz; and a microwave applicator connected to said generator for emitting microwaves to a localized area on a body, wherein said applicator comprises inner conductor means and outer conductor means for maintaining screening structure.

7. The apparatus of claim 6 wherein said generator further comprises:

a microstrip impedance transformer connected between said oscillators and said applicator, the width of said transformer decreasing exponentially from the end adjacent said oscillator to the end adjacent said applicator.

8. A microwave apparatus for regulating physiological functions of human and animal bodies, comprising:

a microwave generator and a microwave applicator connected to said generator for emitting microwaves to a localized area on a body, wherein said applicator comprises an inner conductor formed from a metal bar connected at one end thereof to the output line of said generator, the other end thereof serving as a physiotherapeutic head, said physiotherapeutic head being separable from and fixable to said inner conductor, and an outer conductor connected at one end thereof to the ground of said generator and opened at the other end thereof, said inner conductor being held inside the structure of the outer conductor, said outer conductor being designed such that both of said conductors maintain direct contact with the skin during treatment, said outer conductor further serving as a screening structure.

9. The apparatus of claim 8 wherein said physiotherapeutic head is connected elastically to said inner conductor and can make axial elastic movement relative to said inner conductor.

10. The apparatus of claim 8 wherein said inner conductor is of a hollow structure capable of receiving the handle of an acupuncture needle when said physiotherapeutic head is removed, and of forming a capacitive coupling with said handle during treatment while keeping said outer conductor in contact with the skin.

11. An apparatus for regulating physiological functions of a human body using localized microwave irradiation, comprising:

(a) a microwave generator comprising a plurality of oscillators connected in parallel, a microstrip impedance transformer having a width which decreases exponentially, and a metal housing serving as a screen and a heat sink, wherein the side end of said transformer is connected to the output of said oscillators;

(b) a microwave applicator which comprises an inner conductor formed from a metal bar, a screening outer conductor, and a base, wherein one end of each of said conductors is fixed on said base, said conductors being insulated from each other, the end of said inner conductor remote from said base having a detachable physiotherapeutic head and that of said outer conductor forming an open end, the width of said outer conductor increasing exponentially from said base end to said open end, said physiotherapeutic head and said open end lying in substantially the same plane; and (c) a coaxial cable having its inner conductor connected respectively to the narrow end of said impedance transformer and to said inner conductor of said applicator, and its outer conductor connected respectively to said metal housing of said generator and said outer conductor of said applicator.

* * * * *